United States Patent

Cohn et al.

[11] Patent Number: 5,825,485
[45] Date of Patent: Oct. 20, 1998

[54] COMPACT TRACE ELEMENT SENSOR WHICH UTILIZES MICROWAVE GENERATED PLASMA AND WHICH IS PORTABLE BY AN INDIVIDUAL

[76] Inventors: Daniel R. Cohn, 26 Walnut Hill Rd., Chestnut Hill, Mass. 02167; Paul Woskov, 4 Ledgewood Dr., Bedford, Mass. 01730; Charles H. Titus, 323 Echo Valley La., Newtown Square, Pa. 19073; Jeffrey E. Surma, 806 Brian La., Kennewick, Wash. 99337

[21] Appl. No.: 552,677

[22] Filed: Nov. 3, 1995

[51] Int. Cl.$^6$ .................................. G01J 3/30; H01P 1/00; G01N 21/69
[52] U.S. Cl. ........................................ 356/316; 333/99 PL
[58] Field of Search ......................... 356/316; 333/99 PL

[56] References Cited

U.S. PATENT DOCUMENTS

| | | |
|---|---|---|
| 3,554,648 | 1/1971 | Boostrom et al. . |
| 5,262,610 | 11/1993 | Huang et al. . |
| 5,479,254 | 12/1995 | Woskov et al. ........................ 856/316 |

OTHER PUBLICATIONS

Fehsenfeld, "Microwave Discharge Cavities Operating at 2450 MHz", The Review of Scientific Instruments, vol. 36, No. #3 Mar. 1968, pp. 294–298.
Bacharach Instrument Co (Pittsburg, Pa), Produce description for "J–W Mercury Vapor Sniffer", No date.

Primary Examiner—K. Hantis
Attorney, Agent, or Firm—Choate, Hall & Stewart

[57] ABSTRACT

A method and portable apparatus for self-powered, sensitive analysis of solid, liquid or gas samples for the presence of elements is provided. The apparatus includes a compact sensor system which utilizes a microwave power source and a shorted waveguide to induce a plasma. The microwave power source may be a magnetron or the like. The device includes a portable power supply and preferably includes a portable battery charger. The portable power supply includes a compact generator- internal combustion engine unit. The device can be operated by directly using power from the portable power supply or in a more compact embodiment by using power from batteries that are recharged by a separate portable power supply module. Pulsed microwave operation can be used to reduce average power requirements and facilitate the use of very compact units using batteries. The device is capable of being transported to and from remote sites for analysis by an individual without the need for heavy transportation equipment. A computer may be utilized to control the portable power supply, the battery charger and the microwave power source. The method and apparatus are capable of analyzing samples for the presence of several elements simultaneously using fiber optic guides and a spectrometer system. The apparatus can be contained in a plurality of readily detachable modules to facilitate transportation and field operation.

46 Claims, 4 Drawing Sheets

COMPACT TRACE ELEMENT SENSOR WHICH UTILIZES MICROWAVE GENERATED PLASMA AND WHICH IS PORTABLE BY AN INDIVIDUAL

TECHNICAL FIELD

The present invention generally relates to methods and apparatus for analyzing solids, liquids and gases for the presence of several trace elements simultaneously and more particularly to methods and apparatus for analyzing solids, liquids and gases for several valuable or hazardous trace elements simultaneously using compact, portable trace element sensor devices which are portable by an individual.

BACKGROUND OF THE INVENTION

For various undertakings such as prospecting and mining operations, national security searches for dangerous materials, and assessments of environmentally harmful substances, it is necessary to analyze solids, liquids and gases to detect the presence of valuable or hazardous elements. It is desirable to utilize a sensor device which would be capable of sensitive, real time elemental analysis to monitor or detect the presence of such elements. It is also desirable that such a sensor device be self-powered and sufficiently compact so as to be portable by an individual. In particular, a portable sensor device would facilitate elemental analysis at particular locations, thereby eliminating the need for special sample preparation and the necessity for sending samples to specially equipped laboratories. It is desired that such a sensing device be able to readily detect the presence of valuable elements such as gold, silver, palladium, platinum, and others. It is also desirable that such a device be able to readily detect the presence of hazardous elements such as trace metals including lead, mercury, arsenic, beryllium, chromium, antimony, barium, cadmium, thallium, nickel and selenium. Such a device should have high sensitivity to facilitate discovery of valuable mineral deposits. The device should also require minimal sample preparation to be effective in the field. Such a device should also be capable of detecting the presence of many different elements simultaneously.

Instrumentation and devices for the sensitive elemental analysis of materials developed to date suffer from limitations of their not being compact, portable devices, or being severely limited in terms of the range of elements and forms of matter that can be sampled. The use of plasma sources for elemental excitation or detection is currently the primary means for sensitive detection of trace elements in solids, liquids and gases. M. W. Blades et al., *Application of Weakly Ionized Plasmas for Materials Sampling and Analysis*, IEEE Trans. on Plasma Sci., Vol. 19, pp. 1090–1113 (1991) have reviewed such technology, which included conductively coupled plasmas, microwave-induced plasmas, and other techniques. None of the techniques so described are applicable to sensitive, real time measurements for use in a portable sensor device. Fast Fourier transform spectroscopy, as described by J. Demirgian, *Continuous Monitor for Incinerators*, U.S. Department of Energy Information Exchange Meeting on the Characterization, Monitoring, and Sensor Technologies, Dallas, Tex. (Jun. 3–4, 1992) can be used for continuous, near real time monitoring of molecular gases, but is not capable of the detection of metals, especially if the metals are in particulate form. Commercial in situ detectors, such as the Bacharach Instrument Company mercury sniffer model MV-2J-W and the Pacific Northwest Laboratory Halo-sniff spectrochemical emission sensor cannot be used as portable units for real time measurements of metals in a wide range of particulate as well as vapor form.

F. C. Fehsenfeld et al., *Microwave Discharge Cavities Operating at 2450 MHz*, Rev. of Sci. Instrm., Vol. 36, pp. 294–298 (1965) described a number of microwave-induced plasma (MIP) resonator cavity structures. One such structure had a built in taper to reduce its height to increase the electric field strength for plasma breakdown. This device was a resonator, not a shorted waveguide. It also included a number of features that limited maximum microwave power, such as a cable connection to the source of such power. None of the devices described by Fehsenfeld et al., are suitable for a portable sensor device.

R. M. Barnes, et al., *Design Concepts for Strip-Line Microwave Spectrochemical Sources*, Anal. Chem., Vol. 62, pp. 2650–2654 (1990) described a shorted strip-line microwave MIP arrangement with a dielectric tube through the device one-quarter wavelength from the shorted end. Again, the features of this device, such as the presence of the strip-line and the cable connection to the source, would limit the maximum power operation of this device. The power limit would prevent use in the high power mode which may be desirable for spectroscopic analysis of particulates and would be desirable for a portable device.

H. Matusiewicz, *A Novel Microwave Plasma Cavity Assembly for Atomic Emission Spectrometry*, Spectrachimica Acta, Vol. 47B, pp. 1221–1227 (1992); Y. Okamoto, *Annular-Shaped Microwave-Induced Nitrogen Plasma at Atmospheric Pressure for Emission Spectrometry of Solutions*, Analytical Science, Vol. 7, pp. 283–288 (1991); and D. K. Smith, et al., *Microwave Atmospheric Pressure Plasma Torch, Characteristics and Application*, 27th Microwave Symposium, Washington, D.C. (Aug. 2–5, 1992) described higher power MIP devices connected to the microwave source directly by the waveguide. These devices are unsuitable for use in portable devices.

Other microwave-induced plasma-atomic emission spectroscopy devices are described by K. A. Forbes et al., *Comparison of Microwave-Induced Plasma Sources*, J. of Analytical Atomic Spectrometry, Vol. 6, pp. 57–71 (1991); J. P. Matousek, *Microwave-Induced Plasmas: Implementation and Application*, Prog. Analyt. Atom. Spectrosc., Vol. 7, pp. 2755–314 (1984); S. R. Goode et al., *A Review of Instrumentation Used to Generate Microwave-Induced Plasmas*, Applied Spectrosc., Vol. 38, pp. 755–763 (1984); and Zander et al., *Microwave-Supported Discharges*, Applied Spectrosc., Vol. 35, pp. 357–371 (1981).

It would therefore be desirable to provide methods and apparatus for analyzing solid, liquid and gas samples utilizing a self-powered portable, sensitive trace element sensor device. It would also be desirable to provide a compact, portable sensor device which is capable of characterizing samples containing more than one trace element simultaneously, thereby overcoming the shortcomings associated with the prior art.

SUMMARY OF THE INVENTION

It is an object of the present invention to provide a compact, self-powered portable trace element sensor device.

It is another object of the invention to provide a portable trace element sensor device which can be transported by an individual and without the need for heavy transportation equipment.

It is another object of the invention to provide a portable trace element sensor device which utilizes a microwave induced plasma.

It is another object of the invention to provide a portable trace element sensor device which is capable of utilizing a pulsed or non-pulsed microwave source to achieve high peak powers without requiring a large power supply.

It is yet another object of the invention to provide a portable trace element sensor device which is capable of analyzing solid, liquid or gas compositions.

It is yet another object of the invention to provide a portable trace element sensor device which is capable of analyzing solid, liquid or gas compositions for the presence of several elements simultaneously.

It is still another object of the invention to provide a portable trace element analyzer that does not require sample pretreatment for analysis to speed up and simplify field measurements.

It is still another object of the invention to provide a portable trace element sensor device which is suitable for use in connection with prospecting.

It is still another object of the invention to provide a portable trace element sensor device which is suitable for use in connection with mining.

It is still another object of the invention to provide a portable trace element sensor device which is suitable for use in connection with on site analysis of hazardous elements.

It is still another object of the invention to provide a portable trace element sensor device which is suitable for use in conjunction with various national security applications such as smuggling of weapons materials.

It is still another object of the invention to provide a portable trace element sensor device which includes a portable power supply circuit using electrical power from a compact generator-internal combustion engine system.

It is still a further object of the invention to provide a compact, portable sensor device which can be operated on batteries alone.

It is still a further object of the invention to provide a portable sensor device which includes a portable battery charger module which can be separated from the rest of the device.

It is a further object of the invention to provide a method of analyzing a solid, liquid or gas sample for several trace elements simultaneously using a portable trace element sensor device.

These and other objects of the invention are provided by a portable trace element sensor device which utilizes sensitive, real time elemental analysis at low cost without the necessity for special sample preparation. Preferably, the sensor device is self-powered and is sufficiently compact so as to allow transportation of the device by an individual, thereby eliminating the need for heavy transportation equipment. Power for the device would be supplied by a generator driven by a small internal combustion engine, or rechargeable batteries. For example and while not meant to be limiting, one embodiment of the invention may employ several readily connectable modules, each module containing a component or components of the device therein. The modules are constructed in a manner to facilitate connection with another module or modules at or near the location of the sample to be analyzed. Each module and component parts therein may weigh for example, up to about 30 pounds, such that the total weight of the device is less than 100 pounds. The portable device of the present invention may be taken into the field for rapid on site measurements. The device is suitable for use in connection with prospecting, mining, on site environmental analysis, and for various national security applications.

The portable sensor device uses a plasma which is induced inside a waveguide which is penetrated by openings in the wall of the waveguide such that gas flows through the waveguide transverse to the direction of the microwave power propagation. In a preferred embodiment, the gas flow is confined within a tube formed of dielectric material which is transparent to the microwaves.

The device also includes a microwave power source such as a magnetron, radar source or the like. The microwave power source can be operated in a pulsed or non-pulsed mode to minimize average power requirements and facilitate a relatively low weight, portable design. While not to be construed as limiting, the detection system preferably weighs less than a total of about 200 pounds and more preferably less than 100 pounds. The microwave power source may be connected to a portable power supply having filament and anode sections. The microwave source uses a low voltage, high current filament supply and a high voltage, lower current anode supply to allow for the desired pulsed or continuous operation.

In a preferred embodiment, the unit includes a light weight battery charging system. Compact units can be designed to operate on rechargeable batteries, thereby facilitating operation by reducing size and weight without the generator or internal combustion engine unit.

An exhaust pump or source of compressed gas is utilized to establish flow of solid, liquid or gas compositions through the plasma for elemental analysis. Fiber optic guides transmit the plasma light to a spectrometer system for identification by line spectra of element or elements present in the sample being analyzed. In a preferred embodiment, multiple fibers and spectrometers may be employed to monitor or detect simultaneously many elements present in a sample.

In a preferred embodiment of the invention, a portable computer controls the spectrometer system, monitors forward and reflected power detectors associated with the microwave source, displays spectra and provides compositional analysis of the sample being analyzed. It is also preferred that the computer control the operation of the microwave source.

The foregoing has outlined some of the more pertinent objects of the present invention. These objects should be construed to be merely illustrative of some of the more prominent features and applications of the invention. Many other beneficial results can be attained by applying the disclosed invention in a different manner of modifying the invention as will be described. Accordingly, other objects and a fuller understanding of the invention may be had by referring to the following Detailed Description of the Preferred Embodiments.

BRIEF DESCRIPTION OF THE DRAWINGS

For a fuller understanding of the present invention, reference is had to the following description taken in conjunction with the accompanying drawings, in which.

Similar reference characters refer to similar parts throughout the several views of the drawings.

DETAILED DESCRIPTION OF THE PREFERRED EMBODIMENTS

Figure 1:
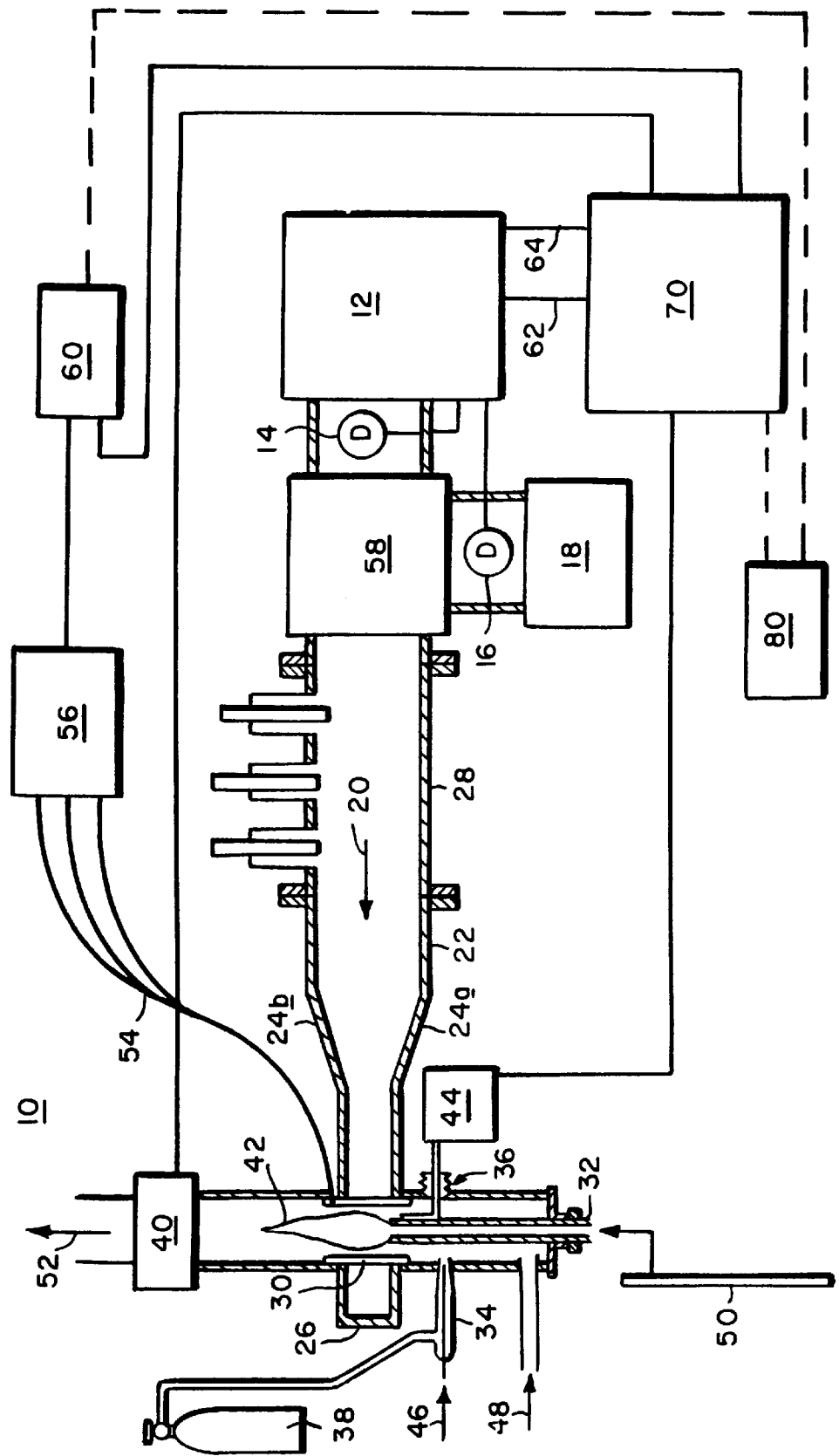
FIG. 1 illustrates a portable microwave plasma torch element sensor device in accordance with the present invention.

The present invention provides a portable trace element sensor device which is capable of sensitive, real time elemental analysis of a solid, liquid or gas sample at low cost without the need for special sample preparation. The sensor device is self-powered and can be transported by an individual, thereby eliminating the need for heavy transportation equipment. For example and while not meant to be limiting, one embodiment of the invention may employ several readily connectable modules, each module containing a component or components of the device therein. The modules are constructed in a manner to facilitate connection to another module or modules at or near the location of the sample to be analyzed (see e.g., FIG. 4). Each module and component parts therein may weigh for example, tip to about 30 pounds, such that the total weight of the device is less than 100 pounds. The modules can be transported by an individual by hand carrying the modules, or by employing a dolly or the like. In this manner, the portable device of the present invention may be taken into the field for rapid on site measurements. The device is capable of being designed for use in connection with prospecting, mining, on site elemental analysis and for various national security applications. The present invention also provides a method for analyzing samples for the presence of trace elements using a portable trace sensor device.

As mentioned above, the compact and portable features of the present invention facilitate use of the device in a variety of different applications. For example, a miner or prospector equipped with such a device would be more efficient in locating valuable ores. The efficiency and cost effectiveness of gold and silver mining in shaft mines would dramatically increase by using such a device to determine which ores contain sufficiently high amounts of gold or silver to send up the shaft to the surface of the earth. In addition, a much more detailed analysis of mines and remote sites may be undertaken utilizing the device of the present invention, thereby insuring that potentially valuable strikes are not surpassed. In addition, extremely compact units may use higher frequency microwave components, e.g. greater than 2.45 GHz, resulting in much smaller sizes and further facilitating their use at remote sites and the like. The sensor device is also capable of being self-powered. Alternatively, the device may be plugged into existing power sources to further reduce size when the unit is used within or near a building, vehicle or the like.

National security is another example of the type of application which would have use for the present invention. Because the device provided by the present invention is capable of making very sensitive measurements, e.g. in a one part per billion range for most elements, it would be valuable to government enforcement agencies for monitoring dangerous substances and the like.

Evaluation on site for harmful pollution exemplifies yet another application for the use of the device provided by the present invention. The portable device of the present invention may be employed to facilitate the characterization of waste sites, analyze water sources for pollution, and monitor industrial sites for hazardous emissions. The device of the present invention thus provides a valuable tool for any industry, community, or groups and other entities concerned with the environment.

Referring now to FIG. 1, a portable microwave plasma torch element sensor device 10 in accordance with the present invention is illustrated. While not to be construed as limiting, it is expected that a portable trace element sensor device in accordance with the present invention will weigh approximately 50–200 pounds and preferably less than 100 pounds. Microwave waveguide 22 propagates power from microwave power source 12. Plasma 42 is induced by waveguide 22 which is penetrated by openings in the walls of waveguide 22 such that plasma gas flows transverse to the direction of microwave power propagation 20 in waveguide 22. In a preferred embodiment, waveguide 22 includes shorted end 26 and tapers 24a, 24b where the plasma is induced from the design of waveguide 22. Tapers 24a, 24b intensify the electric field and facilitate plasma breakdown.

Waveguide 22 may also include impedance matching waveguide section 28, which provides maximum transfer of energy from microwave power source 12 through waveguide 22 to plasma 42 by minimizing reflection. The openings in the waveguide walls are smaller than one quarter of the microwave wavelength and the gas flow passage through waveguide 22 is preferably lined with dielectric material or liner 30 which is transparent to the microwaves. While not meant to be limiting, dielectric materials such as boron nitride or fused quartz are suitable for use in the present invention.

The portable trace element sensor devices in accordance with the present invention utilize a high-power microwave plasma for atomic emission spectroscopy of solid, liquid or gas samples that are entrained in the gas flow through the plasma. In contrast to present microwave plasma spectrometer systems used in laboratories, the portable microwave plasma trace element sensor of the present invention can use a pulsed or continuous microwave source. The use of pulsed operation allows the device to achieve high peak powers without the larger power supply requirements of a continuous power supply. The combination of pulse lengths and pulse repetition rates may be such that a low average power supply may be used (1 to 100 watts) in order to keep the device compact and portable. Alternatively, the microwave source may operate in a non-pulsed mode with a higher capacity power supply system.

As further illustrated in FIG. 1, microwave power source 12 includes forward power detector 14 and reflected power detector 16. Microwave power source 12 may be a magnetron or the like. One class of microwave sources, such as magnetrons used in typical kitchen microwave ovens and the like, may achieve peak powers of about 200 to 2000 watts with average pulse lengths in the 0.01 to 1 second range. The pulse repetition rate may be one pulse per second or longer. Another class of microwave sources, such as those used in radar, may achieve peak powers reaching $10^6$ watts with pulse lengths on the order of approximately $10^{-6}$ seconds. The pulse repetition rate in this case may be up to about 100 per second. In either embodiment, the average power requirement may be relatively low, i.e. in the 1–100 watt range. In a preferred embodiment, microwave power source 12 is connected to portable power supply 70 having filament 62 and anode 64 connections. Reflected power dump 18 is connected to circulator 58 as illustrated in FIG. 1. Portable power supply 70 is connected to computer 60, which preferably is connected to portable battery charger 80. Portable power supply 70 is also connected to exhaust pump 40 as shown in FIG. 1.

The portable unit may also be operated with a microwave tube filament that is continuously on (to reduce wear) while the main microwave power source operation is in a pulsed mode. It may also be desirable to use continuous microwave tube operation; however, the operator would then have to transport a larger power supply unit at all times.

Exhaust pump 40 or compressed gas 38 may be used to establish entrained sample flow through plasma 42 of waveguide 22. Samples may be introduced into plasma gas flow 42 as liquid through liquid sample input 46 and nebulizer 34 as shown in FIG. 1. Alternatively, samples may be introduced into plasma gas flow 42 as solid particulates which can be placed on the end of a graphite dielectric rod subsystem 50 or the like and inserted into plasma flame 42 through dielectric tube 32 which is proximate to the base of flame 42. While not meant to be limiting, alumina or other ceramic tubes topped with a spectrographic graphite rod are suitable for use as sample rods according to the present invention. In yet another alternative embodiment of the invention, samples may be introduced into plasma gas flow 42 as gas via gas sample input 48. Samples which have passed through plasma 42 exit device 10 as exhaust 52, and may subsequently be treated using appropriate measures.

Solid sample quantities of less than about one milligram would be sufficient for analysis. If a solid sample requires size reduction, a small hand held size reduction device can be utilized to reduce the size of the particles. For example, solid samples can be reduced to particulates by a simple hand carried grinder prior to inspection in the microwave plasma device. If the solid sample is in the correct particle size range, the sample may be analyzed directly.

An electrical starting circuit incorporated into the present invention facilitates reproducible restart of the microwave plasma with each pulse. As shown in FIG. 1, high voltage starter 44 is incorporated into device 10 in order to produce a spark or corona to reproducibly restart the plasma during pulsed operation with microwave power levels that are too low to initiate a plasma breakdown, i.e., less than about 10 kW. Starter 44 may be a Telsa coil, an automotive ignition coil or the like. The entry of the starter graphite plasma arc into device 10 is well insulated using insulator 36 or the like so that sparking occurs at the tip nearest the base of plasma 42. A grounded wire point may be positioned near plasma arc starter to facilitate sparking. Starter 44 may be connected to portable power supply 70.

As a sample passes through plasma 42, fiber optic guides 54 transmit the plasma light to spectrometer system 56 (such as a Czemy Turner grating configuration) which identifies the element or elements present in the plasma gas flow by the line spectra of the respective element or elements present in the sample. The fiber optic guides penetrate through the dielectric liner 30 so their light collection efficiency is maximized and their ends are exposed to the plasma flame heat and gas flow to keep them clean. Multiple fibers and spectrometers may be employed to monitor as many elements as needed simultaneously for characterization of a particular site. Simple interference filters with a single detector per element may also be used to simplify the light analysis in certain applications and to facilitate a more compact design.

Portable computer 60, preferably with its own rechargeable battery pack, may control spectrometer system 56, monitor detectors 14, 16, and display the spectra. Portable computer 60 may also be programmed to provide a compositional analysis of the sample being studied. Computer 60 may further be utilized to control the operation of microwave source 12 through a connection to portable power supply 70.

As discussed herein, portable power supply 70 for powering microwave source 12, starter 44, and exhaust pump 40 preferably utilizes rechargeable batteries with appropriate electronics to provide the proper voltages to the various subsystems of portable element sensor device 10. A portable battery charger 80 may be utilized to recharge computer 60 and portable power supply batteries as needed. Exemplary embodiments of the portable power supply 70 and charger 80 will be now be discussed.

Figure 2:
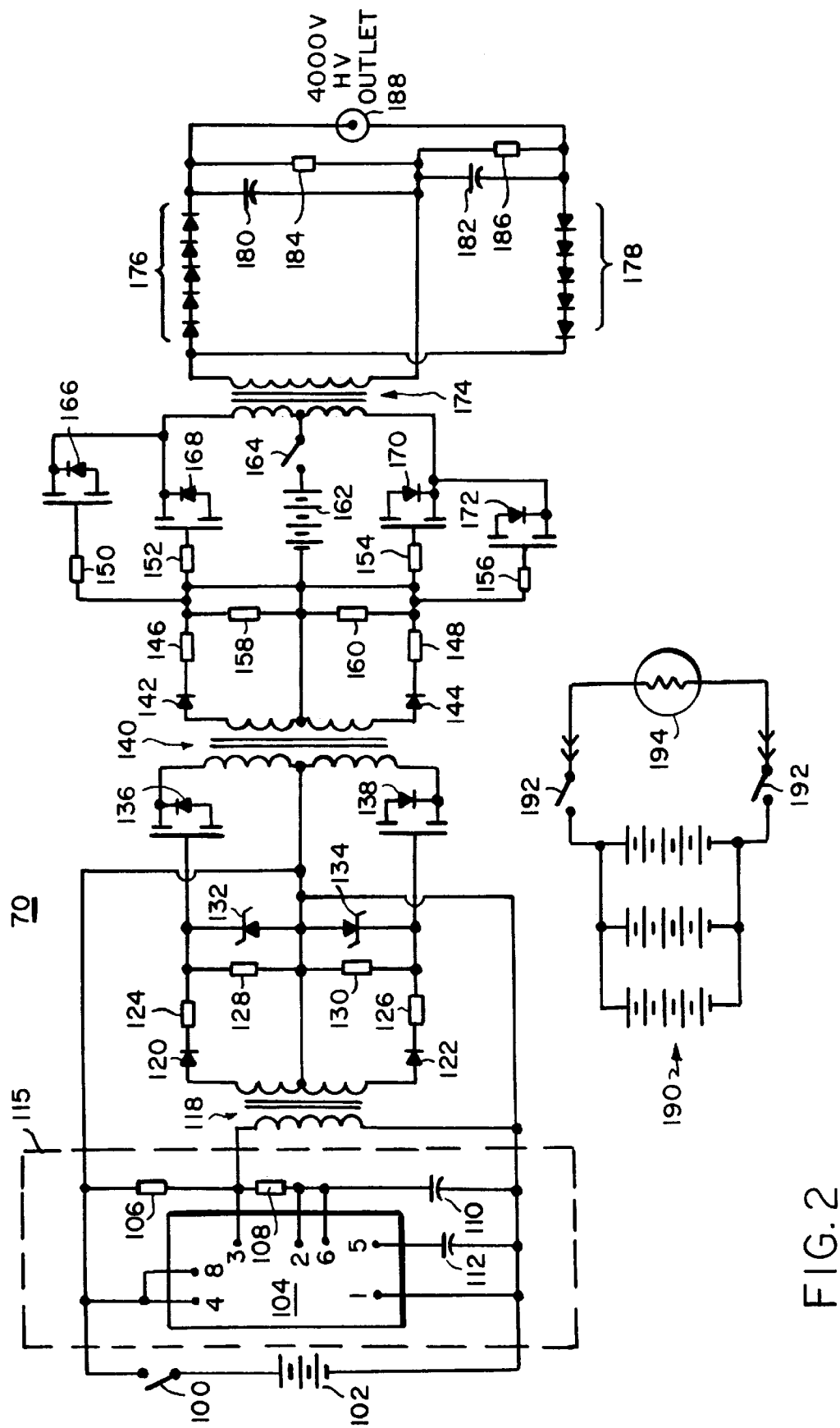
FIG. 2 illustrates a portable power supply circuit suitable for use in conjunction with the microwave plasma torch element sensor device illustrated in FIG. 1.

Referring now to FIG. 2, a portable power supply circuit 70 that is suitable for use in accordance with the present invention is shown. The power supply that is used in accordance with present invention is compact and is capable of employing a different source of electricity in contrast to electricity from a wall plug as is used by current devices. In addition, the associated battery charger 80 (see FIG. 3) provides a compact source of energy.

For purposes of illustration, portable power supply 70 in FIG. 2 depicts a magnetron microwave source which utilizes a low voltage, high current filament supply and a high voltage, lower current anode supply. The voltage/current parameters used are appropriate for a magnetron tube that is commonly used in conventional microwave ovens in kitchens. It should be appreciated, however, that other microwave sources are suitable for use in the present invention. Such a tube may be readily adapted for use in connection with the portable trace element sensor device of the present invention. This type of power supply also uses relatively light weight, rechargeable nickel-cadmium, metal hydride or lithium batteries.

Figure 3:
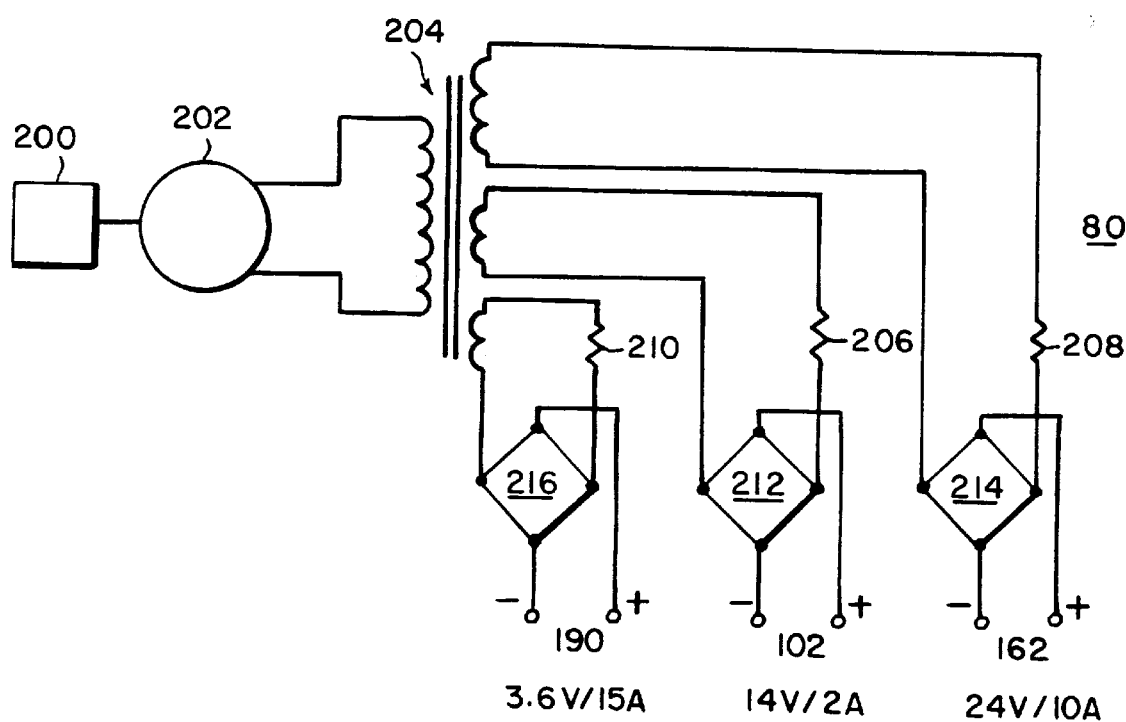
FIG. 3 shows a portable battery charger suitable for use in conjunction with the microwave plasma torch element sensor device illustrated in FIG. 1.

Preferably, power supply circuit 70 is capable of delivering 4000 volts DC at 200 milliamperes for one-second intervals repeatedly at minimum intervals of 30 seconds to magnetron anode 64. Under these conditions, a fully charged battery 162 preferably provides at least about 300 tests prior to discharge. In one embodiment, battery 162 is a 24 volt battery capable of being fully recharged in about 6 hours at a rate of 6 amperes. Batteries 102 and 190 are also preferably designed so as to be capable of being recharged simultaneously with battery 162 using the same battery charger (such as the type of battery charger 80 as shown in FIG. 3).

Battery power sources 102, 162 and 190 preferably are mounted in the same enclosure and designed so that a fully charged spare battery set may be readily connected to power the portable trace element sensor 10. As illustrated in FIG. 2, battery 102 supplies power through switch 100 to the square wave oscillator circuit 115. In one embodiment of the invention, oscillator circuit 115 comprises an oscillator integrated circuit chip 104, such as a 555, connected to resistors 106, 108 and capacitors 110, 112 which determine the interval and period for the generated square wave.

The signal generated by oscillator 115 is fed through isolation transformer 118 whose outputs are connected through diodes 120 and 122 and resistors 124 and 126 for rectification and isolation. Resistors 124 and 126 are further connected to resistors 128 and 130 prior to connection to zener diodes 132 and 134. Zener diodes 132 and 134 regulate the voltage levels fed into the next amplification stage.

The voltage waveforms found on zener diodes 132 and 134 are fed to HEXFETS 136 and 138 respectively. HEXFETS 136 and 138 amplify the signal and are utilized to drive step-up transformer 140. The output of step-up transformer 140 is further connected through an isolation rectification circuit comprising diodes 142 and 144 with resistors 146, 148 (and resistors 158 and 160), as found connected to the output of transformer 118. The signals thus generated are used to drive HEXFETS 166, 168, 170, and 172 through resistors 150, 152, 154 and 156, respectively. The 30 kilohertz square wave is supplied through transformer 118 to the gates of HEXFETS 136 and 138 which in turn power the gates of HEXFETS 166, 168, 170 and 172. It should be appreciated that while FIG. 2 illustrates two HEXFETS in parallel, three or four HEXFETS may be used in parallel to conserve power from battery 162. Using an intermediate set of HEXFETS (136 and 138) to drive the higher power HEXFETS (166, 168, 170 and 172) facilitates a more efficient power supply design. HEXFETS 166, 168, 170 and 172 are utilized to drive the final transformer 174.

Battery 162 provides a source of energy for the anode 64. For example, energy from battery 162 may be converted to about 4000 DC for the anode 64. Switch 164 provides a control for turning the anode on and off. While not intending to be limiting, switch 164 can be controlled by computer 60.

Final transformer 174 is connected through diode chains 176 and 178, to capacitors 180 and 182 and resistors 184 and 186 respectively, which rectify and smooth the voltage waveform outputted by transformer 174. The power supply voltage is then presented to connector 188 for supply to the microwave generator.

Transformer 174 is a high frequency, high voltage power transformer which is preferably both compact and light weight. The input is the HEXFET (166, 168, 170, 172) switched 24 volts from battery 162 and is stepped up to 2000 volts, square wave by transformer 174 which operates at 30 kilohertz.

In one embodiment of the invention, diodes 176 and 178 each include five 1000 volt, 2.5 amperes diodes connected in series. Capacitors 180 and 182 are each rated at least 3000 volts DC and have a capacitance of 0.1 microfarad. Resistors 184 and 186 are each 20 megaohms 1 watt and will discharge capacitors 180 and 182 in less than 10 seconds after power is shut off. The circuit which includes the secondary winding of transformer 174, diodes 176 and 178, and capacitors 180 and 182 is a conventional voltage doubling circuit. It will be appreciated by those skilled in the art, however, that the particular embodiments of the invention described are shown by way of illustration and not as limitations of the invention. The principle features of this invention can be employed in various embodiments without departing from the scope of the invention. For example, diodes 176 and 178 can each include a 5000 volt diode rather than five 1000 volt diodes.

The 3.3 volt, 10 amperes filament power 194 for magnetron 12 can be provided in the most efficient manner utilizing a series-parallel connection of 9 size D industrial type nickel-cadmium batteries.

The operation of the power supply circuit 70 will now be described. Switch 192 is closed first for at least one minute in order to properly heat magnetron filament 194 and obtain several analyses of the material being tested. If the magnetron filament current is not manually turned off in approximately three minutes, an automatic timing circuit will shut off filament power and prevent undesirable discharge of the batteries. Alternatively, if the batteries are sufficiently robust, the filament can be left on for all sample pulses to increase filament life time. Switch 100 is closed next, thereby initiating oscillator integrated circuit chip 104 and providing 30 kilohertz square wave pulses to all of the HEXFETS gates. The magnetron anode power 188 is turned on by closing switch 164 which in turn starts a one-second timer. At the end of the one second, anode power is turned off. By opening switch 164 and waiting for at least 30 seconds, the anode circuit may be reenergized by closing switch 164 and analyzing another sample.

Referring now to FIG. 3, a simple, light weight portable battery charging system 80 which includes a small, light weight gasoline engine generator 200. An engine capable of generating about one kilowatt is suitable for use in accordance with the present invention. For example, internal combustion engines such as the those used with a "WEED WACKER"™, a leaf blower or a chain saw are suitable for use. The engine is directly connected to a small alternator 202. Alternators of the type used in a motorcycle, a small automobile or the like are suitable for use in accordance with the present invention. Alternator 202 may be a single, two-phase or three-phase alternator. The alternator stator may be rewound to provide three separate windings with an appropriately sized full wave bridge rectifier connected to each winding, thereby providing the proper voltage for charging batteries 102, 162 and 190 and the computer battery pack. The device can be powered primarily with the batteries. Alternatively, the device can be powered using the batteries for peak power during pulsing. This can be accomplished by providing an engine 200 and an alternator 202 of sufficient size and capability that the device can be operated in a continuous mode without reducing the ampere-hour capacity or energy storage capacity of the batteries (when the batteries are used alone).

It is also possible to rewind the alternator stator for single-phase or two-phase operation and then use a transformer such as transformer 204 shown in FIG. 3 to provide the proper DC voltage for each of the four batteries. Transformer 204 is preferably a small higher frequency transformer. In one embodiment of the invention, inductors 206, 208 and 210 may be employed to limit DC current and improve battery charging characteristics. In this embodiment, rectifiers 212, 214 and 216 are connected to inductors 206, 208 and 210, respectively. Rectifiers 212, 214 and 216 are connected to batteries 102, 162 and 190, respectively.

Figure 4:
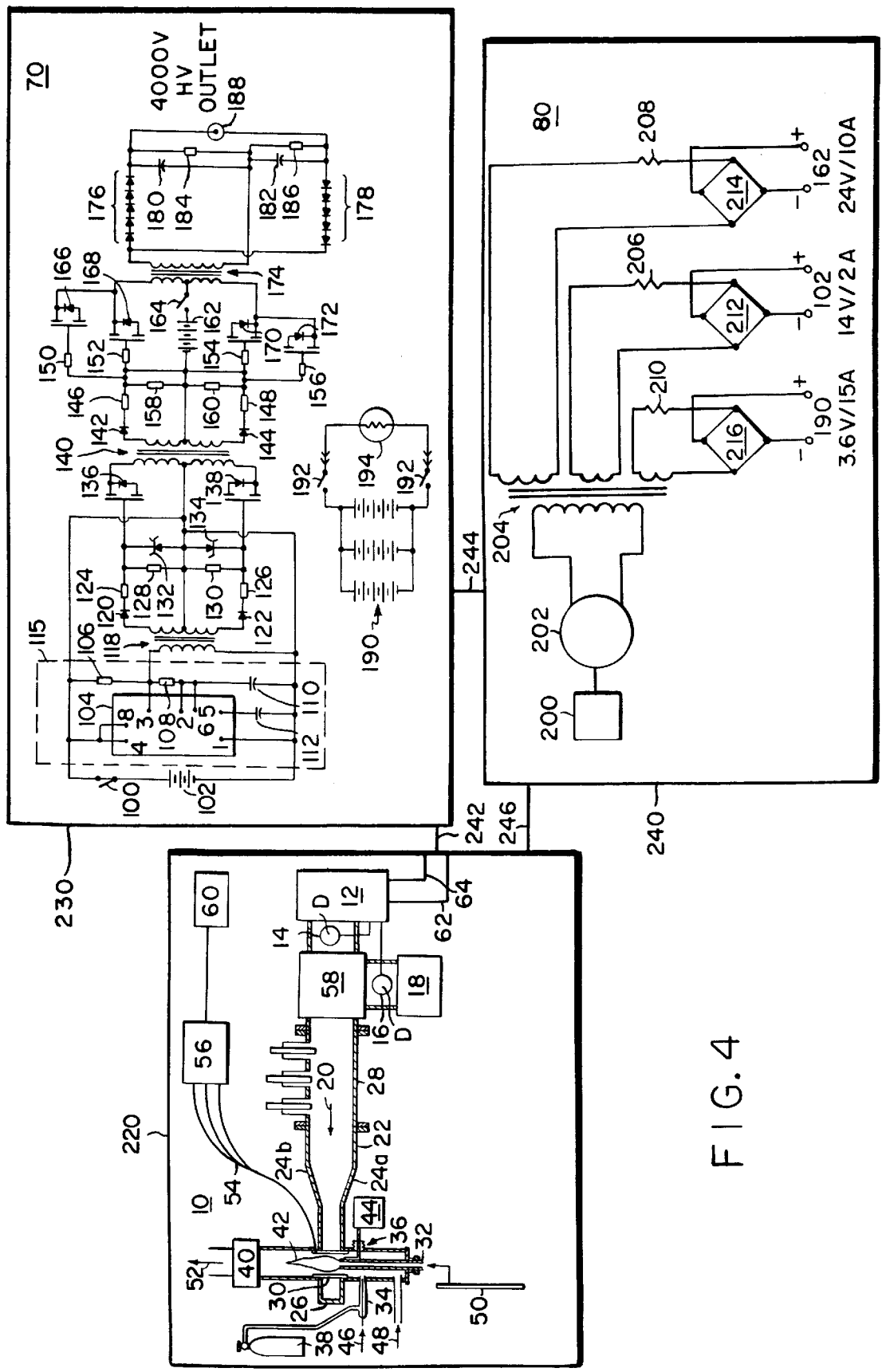
FIG. 4 illustrates a modular arrangement in accordance with one embodiment of the present invention.

The features of the portable microwave plasma torch element sensor device 10 described above allow the plasma torch to be portable and compact, i.e., on the order of the size of the waveguide. In this manner, the device may be transported from site to site by an individual without the need for heavy or large equipment. FIG. 4 is an exemplary illustration of the compact and portable features of the invention. The modular arrangement illustrated in FIG. 4 contains three modules 220, 230 and 240. Module 220 contains the plasma torch with the optical sensor in addition to the computer. As further shown in FIG. 4, module 230 contains power supply circuit 70 and module 240 contains battery charger 80. The modules are connected by cables 242, 244 and 246. Cable such as coaxial cable is suitable for use in accordance with the present invention. It will be appreciated by those skilled in the art that the modular arrangement shown in FIG. 4 is exemplary and can be modified in accordance with the present invention. The modular arrangement facilitates transportation and ease of operation of the device. For example, transportation of a plurality of modules (using a dolly or the like) allows the device to be readily transported through airports, to and from field sites, and the like. Ease of operation is facilitated with the use of the cables to connect the modules at a particular site. In some instances, it may be desirable to adjust the cable lengths such that one or more modules can be placed in close proximity to the sample to be analyzed while the other module or modules are placed a further distance from the sample to be analyzed. For example, space restrictions may make it desirable to take a module containing the plasma torch with the optical sensor into a mine shaft while leaving the other module or modules at the surface of the earth. The modules can be connected by the cables so that samples can be analyzed as previously described.

In addition, the sensor device of the present invention provides a plasma torch which is safe from microwave leakage to the operator. This can be attributed at least in part to the waveguide openings being small relative to the wavelength. Moreover, the portable sensor device provides a plasma torch which is robust as a result of the microwave power density being maximized by tapering of the waveguide.

The compact portable microwave plasma torch system of the present invention provides distinct advantages over the prior art. It differs significantly from relatively large microwave induced plasma systems used in the laboratory. See e.g., Zander et al., *Microwave-Supported Discharges*, Applied Spectroscopy, Vol. 35, p. 357 (1981); Forbes, et al., *Comparison of Microwave-Induced Plasma Sources*, Journal of Analytic Atomic Spectrometry, Vol. 6, p. 57 (1991), both of which are incorporated herein by reference. It also differs significantly from in furnace off gas analysis applications.

Another advantage associated with the present invention will be the ability to accept samples for analysis without special preparation, regardless of whether the sample is in a solid, liquid or gas state. Existing laboratory units are generally designed to accept only one of these states in a specially prepared matrix.

It should be appreciated by those skilled in the art that the specific embodiments disclosed above may readily be utilized as a basis for modifying or designing other methods or structures for carrying out the same purpose of the present invention. It should also be realized by those skilled in the art that such equivalent constructions do not depart from the spirit and scope of the invention as set forth in the appended claims.

What is claimed is:

1. A self-powered trace element sensor device which is portable by an individual, comprising:
    a microwave energy source;
    a shorted waveguide including an aperture for the passage of samples to be analyzed, the waveguide configured to be connected to the microwave energy source to generate plasma in the aperture in the waveguide;
    means for introducing a solid sample to be analyzed into the aperture in the waveguide, the means for introducing the solid sample configured to be connected to the waveguide;
    means for introducing a liquid sample to be analyzed into the aperture in the waveguide, the means for introducing the liquid sample configured to be connected to the waveguide;
    means for introducing a gaseous sample to be analyzed into the aperture in the waveguide, the means for introducing the gaseous sample configured to be connected to the waveguide;
    a spectrometer configured to be connected to receive light from the plasma; and
    a portable power supply configured to be attached to the microwave energy source;
    wherein the device is configured to be portable by an individual for use at a plurality of locations and for use with a plurality of analysis applications.

2. The portable trace element sensor device of claim 1, wherein the microwave energy source is configured to operate in a pulsed mode of operation.

3. The portable trace element sensor device of claim 2, further including a starter attached to the portable power supply, wherein the starter is configured to produce a spark to initiate the plasma during pulsed operation.

4. The portable trace element sensor device of claim 1, wherein the microwave energy source is configured to operate in a continuous mode of operation.

5. The portable trace element sensor device of claim 1, wherein the portable power supply is connected to the microwave energy source with a filament and an anode.

6. The portable trace element sensor device of claim 5, wherein the filament operates in a continuous mode and the main power for the microwave tube is pulsed.

7. The portable trace element sensor device of claim 1, wherein the portable power supply is configured to be connected to a compact generator- internal combustion engine unit.

8. The portable trace element sensor device of claim 1, wherein the device is contained in a plurality of readily detachable modules.

9. The portable trace element sensor device of claim 8, wherein the number of modules is three, the first module containing the microwave energy source, the shorted waveguide, the spectrometer, the means for introducing a solid sample into the aperture in the waveguide, the means for introducing a liquid sample into the aperture in the waveguide and the means for introducing a gaseous sample into the aperture in the waveguide; the second module containing the portable power supply; and the third module containing one or more rechargeable batteries.

10. The portable trace element sensor device of claim 9, further including a compact generator- internal combustion engine unit in the second module and a fourth module containing a battery charger therein.

11. The portable trace element sensor device of claim 1, further including a portable battery charger configured to be attached to the portable power supply.

12. The portable trace element sensor device of claim 1, wherein one or more rechargeable batteries is configured to provide electrical power for the device.

13. The portable trace element sensor device of claim 12, wherein the rechargeable batteries provide a portion of the electrical power for the device.

14. The portable trace element sensor device of claim 12, wherein the rechargeable batteries provide all of the electrical power for the device.

15. The portable trace element sensor device of claim 1, further including a portable computer configured to be attached to the portable power supply.

16. The portable trace element sensor device of claim 15, further including a portable battery charger configured to be attached to the portable power supply and to the computer.

17. The portable trace element sensor device of claim 1, wherein the device is configured such that solid, liquid or gaseous samples can be directly analyzed without pretreatment.

18. The portable trace element sensor device of claim 1, further including a grinder to reduce the size of the solid sample prior to analysis.

19. The portable trace element sensor device of claim 1, wherein the means for introducing the solid sample includes a dielectric rod configured to support a solid sample to be analyzed thereon and configured such that the solid sample is exposed to the plasma.

20. The portable trace element sensor device of claim 19, further including a dielectric tube configured to be proximate to a base of the plasma and configured such that the dielectric rod can be inserted therethrough.

21. The portable trace element sensor device of claim 1, wherein the device is configured to analyze a plurality of trace elements in a gas sample simultaneously.

22. The portable trace element sensor device of claim 1, wherein the device is configured to analyze a plurality of trace elements in a liquid sample simultaneously.

23. The portable trace element sensor device of claim 1, wherein the device is configured to analyze a plurality of trace elements in a solid sample simultaneously.

24. The portable trace element sensor device of claim 1, further including a pump positioned to facilitate flow of solid, liquid or gas samples through the plasma for analysis.

25. The portable trace element sensor device of claim 1, wherein the means for introducing a liquid sample includes a nebulizer attached to the waveguide.

26. The portable trace element sensor device of claim 1, further including a dielectric liner proximate to the aperture in the waveguide.

27. The portable trace element sensor device of claim 26, wherein the dielectric liner is transparent to microwaves generated by the microwave energy source.

28. The portable trace element sensor device of claim 27, wherein the dielectric liner is formed of boron nitride.

29. The portable trace element sensor device of claim 27, wherein the dielectric liner is formed of fused quartz.

30. The portable trace element sensor device of claim 27, further comprising fiber optic guides for plasma light collection, the fiber optic guides penetrating the dielectric liner.

31. The portable trace element sensor device of claim 1, wherein the microwave energy source is a magnetron.

32. The portable trace element sensor device of claim 1, wherein the microwave energy source is a radar microwave source.

33. A self-powered, portable trace element sensor device, comprising:
   a microwave energy source;
   a shorted waveguide including an aperture for the passage of samples to be analyzed, the waveguide configured to be connected to the microwave energy source to generate plasma in the aperture of the waveguide;
      means for introducing a solid sample to be analyzed into the aperture in the waveguide, the means for introducing the solid sample configured to be connected to the waveguide;
   means for introducing a liquid sample to be analyzed into the aperture in the waveguide, the means for introducing the liquid sample configured to be connected to the waveguide;
   means for introducing a gaseous sample to be analyzed into the aperture in the waveguide, the means for introducing the gaseous sample configured to be connected to the waveguide;
   a spectrometer configured to be connected to receive light from the plasma; and
   a portable power supply configured to be attached to the microwave energy source, wherein the portable power supply operates on batteries; and
   wherein the device is configured to be portable by an individual for use at a plurality of locations and for use with a plurality of analysis applications.

34. A self-powered trace element sensor device, comprising:
   a microwave energy source;
   a shorted waveguide including an aperture for the passage of samples to be analyzed, the waveguide configured to be connected to the microwave energy source to generate plasma in the aperture of the waveguide;
   a dielectric tube positioned such that one end of the of the dielectric tube is proximate to the aperture in the waveguide;
   a nebulizer connected to the shorted waveguide such that liquid samples to be analyzed can be introduced through the nebulizer into the aperture in the waveguide;
   a spectrometer configured to be connected to receive light from the plasma; and
   a portable power supply configured to be attached to the microwave energy source.

35. The device of claim 34, further comprising a sample gas input connected to the waveguide such that the sample gas flows through the aperture in the waveguide.

36. The device of claim 34, further including a dielectric rod configured to be inserted through the dielectric tube and into the plasma.

37. The device of claim 36, wherein the dielectric rod has a graphite sample receptacle.

38. The device of claim of claim 37, further comprising a sample gas input connected to the waveguide such that the sample gas flows through the aperture in the waveguide.

39. The device of claim 34, further including a source of compressed gas connected to the nebulizer.

40. The device of claim 34, further including a dielectric liner proximate to the aperture in the waveguide.

41. The device of claim 35, wherein the dielectric liner is transparent to microwaves generated by the microwave energy source.

42. The device of claim 41, wherein the dielectric liner is formed of boron nitride.

43. The device of claim 41, wherein the dielectric liner is formed of fused quartz.

44. The device of claim 41, further comprising at least one fiber optic guide for plasma light collection, the at least one fiber optic guide penetrating the dielectric liner.

45. The device of claim 34, further comprising at least one fiber optic guide configured to be connected to the spectrometer and configured to transmit plasma light to the spectrometer.

46. The device of claim 45, wherein an end of the at least one fiber optic guide is configured to be exposed to the plasma generated in the aperture of the waveguide.

* * * * *